US010646320B1

(12) United States Patent
Leevy et al.

(10) Patent No.: US 10,646,320 B1
(45) Date of Patent: May 12, 2020

(54) SUBJECT IMAGING BED

(71) Applicants: Warren Matthew Leevy, Granger, IN (US); Lucas Liepert, Granger, IN (US); Nathan Higgins, St. Marys, PA (US)

(72) Inventors: Warren Matthew Leevy, Granger, IN (US); Lucas Liepert, Granger, IN (US); Nathan Higgins, St. Marys, PA (US)

( * ) Notice: Subject to any disclaimer, the term of this patent is extended or adjusted under 35 U.S.C. 154(b) by 955 days.

(21) Appl. No.: 14/641,114

(22) Filed: Mar. 6, 2015

Related U.S. Application Data

(60) Provisional application No. 61/949,764, filed on Mar. 7, 2014.

(51) Int. Cl.
*A61D 7/04* (2006.01)
*A61D 3/00* (2006.01)
(Continued)

(52) U.S. Cl.
CPC .............. *A61D 7/04* (2013.01); *A61B 5/0555* (2013.01); *A61B 6/04* (2013.01); *A61B 19/5225* (2013.01);
(Continued)

(58) Field of Classification Search
CPC ....... A61B 6/04; A61B 6/0407; A61B 6/0421; A61B 6/508; A61B 5/055; A61B 5/0555;
(Continued)

(56) References Cited

U.S. PATENT DOCUMENTS 3,094,101 A * 6/1963 Porter .................. A01K 1/0613
119/473
4,332,244 A 6/1982 Levy et al.
(Continued)

FOREIGN PATENT DOCUMENTS

EP 2095791 2/2019
KR 1020130134699 2/2015
(Continued)

OTHER PUBLICATIONS

Xenogen, XGI-8 Gas Anesthesia System, Product pamphlet obtained from http://www.caliperls.com/assets/015/7293.pdf, copyright 2007 Caliper Life Sciences Inc., obtained from internet Aug. 2, 2019.
(Continued)

*Primary Examiner* — Robert G Santos
(74) *Attorney, Agent, or Firm* — Notre Dame Intellectual Property Clinic

(57) ABSTRACT

An imaging bed for use with test subjects that keeps the subject sedated and warm throughout the imaging process. In embodiments, the bed uses radiant heating or cooling by pushing a heated or chilled fluid through the bed to control the temperature of the test subject during the imaging process. The imaging bed can also incorporate an integrated anesthesia channel. In embodiments, an exhaust channel removes the cool air, as well as the unused anesthesia from the imaging bed though an exhaust port. Various embodiments include a docking mechanism for easy connection of anesthesia to the bed, as well as an adapter for fitting smaller or multiple subjects simultaneously within the imaging bed.

14 Claims, 17 Drawing Sheets

(51) Int. Cl.
*A61B 5/055* (2006.01)
*A61B 6/04* (2006.01)
*A61B 19/00* (2006.01)

(52) U.S. Cl.
CPC .......... *A61D 3/00* (2013.01); *A61B 2019/524* (2013.01); *A61B 2019/5231* (2013.01); *A61B 2019/5236* (2013.01); *A61B 2503/40* (2013.01)

(58) Field of Classification Search
CPC .......... A61D 7/04; A61D 3/00; A01K 1/0613; A01K 1/03; A01K 1/031
USPC .... 5/601, 600, 621, 622, 624; 378/209, 208; 119/417, 420, 752, 755, 756; 600/407, 600/415, 421, 422
See application file for complete search history.

(56) References Cited

U.S. PATENT DOCUMENTS

| | | | |
|---|---|---|---|
| 4,520,808 A | 6/1985 | LaBauve | |
| 4,721,060 A | 1/1988 | Cannon | |
| 5,297,502 A | 3/1994 | Jaeger | |
| 5,626,130 A | 5/1997 | Vincent | |
| 5,896,829 A | 4/1999 | Rothenberg et al. | |
| 6,776,158 B1 | 8/2004 | Anderson | |
| 7,021,483 B2 | 4/2006 | Tack et al. | |
| 7,464,707 B2 | 12/2008 | Dalgetty et al. | |
| 7,503,323 B2 | 3/2009 | Dalgetty | |
| 7,865,226 B2 | 1/2011 | Chiodo | |
| 8,189,737 B2 | 5/2012 | Keller | |
| 8,196,574 B2 | 6/2012 | Ichikawa | |
| 8,342,136 B2 | 1/2013 | Hadjioannou | |
| 8,660,633 B2 | 2/2014 | Zagorchev | |
| 8,851,018 B2* | 10/2014 | Rapoport | A61B 5/0555 119/420 |
| 8,918,163 B2* | 12/2014 | Yared | A61B 6/0421 119/417 |
| 9,408,682 B2* | 8/2016 | Lanz | A61B 5/0555 |
| 9,820,675 B2* | 11/2017 | Rapoport | A61B 5/0555 |
| 2004/0136878 A1 | 7/2004 | Meier et al. | |
| 2009/0043172 A1 | 2/2009 | Zagorchev | |
| 2010/0101500 A1 | 4/2010 | Sannie | |
| 2010/0269260 A1 | 10/2010 | Lanz | |
| 2011/0071388 A1 | 3/2011 | Yared | |
| 2012/0073509 A1* | 3/2012 | Rapoport | A61B 5/0555 119/420 |
| 2012/0278990 A1 | 11/2012 | Lanz et al. | |
| 2014/0069426 A1 | 3/2014 | Houts et al. | |
| 2014/0121493 A1 | 5/2014 | Shi | |
| 2014/0378821 A1* | 12/2014 | Rapoport | A61B 5/0555 600/411 |
| 2014/0378825 A1* | 12/2014 | Rapoport | A61B 5/0555 600/415 |
| 2015/0047724 A1 | 2/2015 | Leevy et al. | |
| 2015/0320534 A1 | 11/2015 | Im et al. | |
| 2015/0327968 A1 | 11/2015 | Im et al. | |
| 2015/0328065 A1 | 11/2015 | Boak | |

FOREIGN PATENT DOCUMENTS

| | | |
|---|---|---|
| WO | WO19999017678 | 4/1999 |
| WO | 1999/043389 | 9/1999 |
| WO | 2007135248 | 11/2007 |
| WO | WO2010002331 | 1/2010 |

OTHER PUBLICATIONS

EZ-Systems, EZ-109 Multi-Animal Breather, https://www.ersystemsinc.com/product/ez-109-multi-breather/ website, copyright 2019 EZ-Systems, obtained from internet Aug. 3, 2019.
Parkland Scientific, Multi Station Surgical Board, parklandscientific.com website, copyright 2019 Parkland Scientific, obtained from Internet Aug. 2, 2019.
Mi Labs B.V., Accessories web page, milabs.com website, copyright 2018 MILabs B.V., obtained from the internet Aug. 2, 2019.
Jun Dazai, Nicholas A. Bock, Brian J. Nieman, Lorinda M. Davidson, R. Mark Henkelman, and X. Josette Chen, Multiple Mouse Biological Loading and Monitoring System for MRI, Magnetic Resonance in Medicine, 2004, 52:709-715 (2004).
Chris Suckow, Claudia Kuntner, Patrick Chow, Robert Silverman, Arion Chatziioannou, and David Stout, Multimodality Rodent Imaging Chambers for Use Under Barrier Conditions With Gas Anesthesia, Mol. Imaging Biol. Mar.-Apr. 2009; 11(2) 100-106.

\* cited by examiner

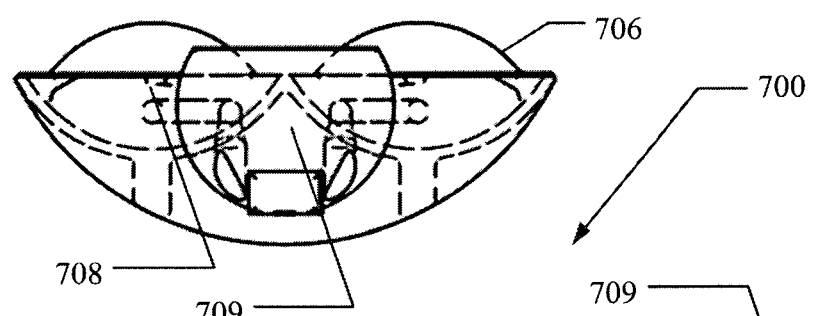
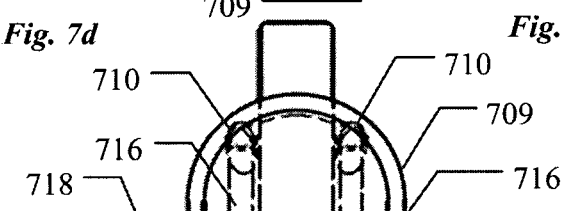
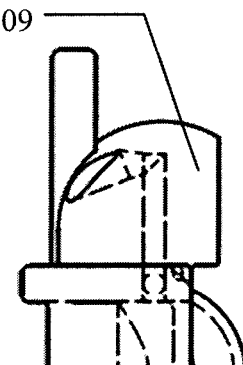
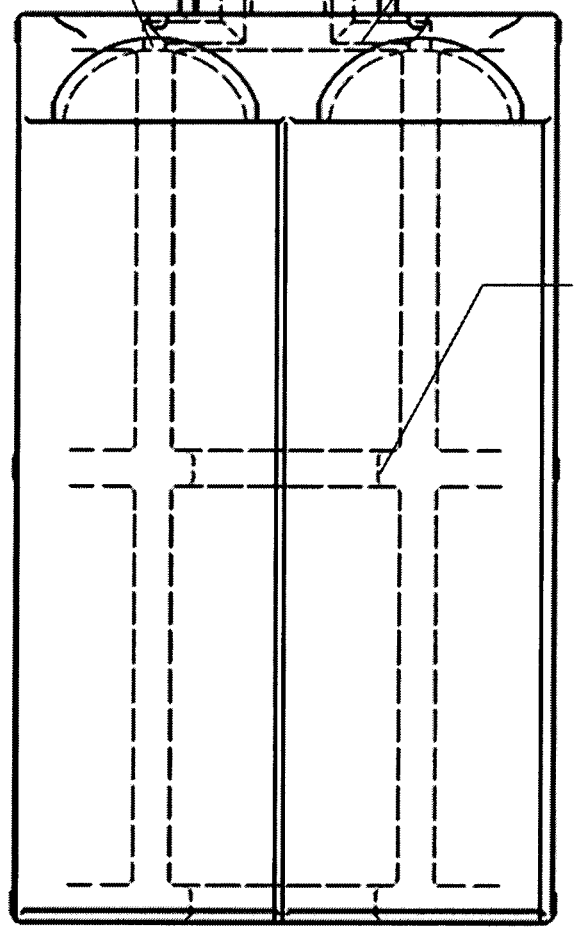

SUBJECT IMAGING BED

CROSS-REFERENCE TO RELATED APPLICATIONS

This application claims the benefit of the filing date of U.S. provisional patent application Ser. No. 61/949,764, filed on Mar. 7, 2014, entitled "In Vivo Imaging Animal Bed with Integrated Anesthesia Delivery, Waste Gas Scavenging, and Heating in One Single Part," the disclosure of which is incorporated herein by reference.

BACKGROUND

In-vivo imaging of animal subjects is a common part research and investigation of the biological functions of subjects. One advantage of in-vivo imaging is the ability to repeatedly scan or image subjects, allowing comparisons over time as well as comparisons between individual subjects. Repeated scanning of a single subject, or a limited set of subjects, facilitates identification of trends and may be more efficient and effective than single instance scanning of numerous subjects. However, comparison of images can be difficult with live subjects as positions may vary from scan to scan and motion of a subject during scanning negatively impacts the resulting images.

In-vivo imaging typically requires the subject to remain motionless during the scanning process, which can take up to an hour or more, depending upon the number and type of images collected. Injected anesthetics may be insufficient to restrain the subject for the entire length of the scanning process. Moreover, injected anesthetics vary in depth over time, which could effect the very biological functions being investigated. Consequently, anesthetic gas or fluid can be used to provide a constant depth of anesthesia to the subject. However, delivery of the anesthetic gas while the subject is within the imaging system poses its own challenges.

Typically, imaging beds are used to position the subject during imaging, providing a consistent platform for the subject. All or a portion of the imaging bed is inserted with the subject in place into the imaging system. As used herein, the term "imaging system" refers to any system used for collecting information about the subject. Imaging systems frequently use an isotope to assist in the creation of an image. Some imaging systems currently in use include, but are not limited to, Positron Emission Tomography (PET), Computerized Tomography, and Magnetic Resonance Imaging (MRI) system, such as the Albira MicroPET, MicroSPECT, Scanlo VivaCT, Bruker and PerkinElmer MR, IVIS optical imaging systems.

BRIEF SUMMARY

The following presents a simplified summary in order to provide a basic understanding of some aspects of the claimed subject matter. This summary is not an extensive overview. It is not intended to either identify key or critical elements or to delineate the scope of the claimed subject matter. Its sole purpose is to present some concepts in a simplified form as a prelude to the more detailed description that is presented later.

An embodiment of a subject imaging bed comprises a base that supports a subject during imaging, the base having a bed surface on which a subject is positioned for imaging and a subject interface connected to the bed surface, the subject interface having an anesthesia outlet. An anesthesia channel integrated in the base directs anesthesia fluid to the anesthesia outlet, and an exhaust inlet in the base located proximate to the subject interface, where an exhaust channel integrated in the base connects the exhaust inlet. A temperature channel integrated in the base and adjacent to a substantial portion of the bed surface, directs a fluid to a temperature control outlet located substantially opposite the subject interface and exhaust inlet.

In embodiments, the temperature channel substantially covers the length and breadth of the bed surface, wherein when the fluid is inserted into the fluid channel, the bed surface is heated by the flow of the fluid through the temperature channel. In other embodiments, the imaging bed includes a fiducial receptacle shaped to support a removable fiducial container loaded with a fiducial marker.

In other embodiments, an apparatus that supports a subject during imaging, comprises a bed including a base having a bed surface on which the subject is positioned for imaging, a subject interface that includes an anesthesia outlet through which anesthesia gas is administered to the subject, and an exhaust inlet located proximate to the subject interface through which exhaust gas is drained from the bed. An exhaust channel is incorporated into the base and connected to the exhaust inlet, wherein the exhaust channel directs the drained exhaust gas from the bed. The apparatus includes a removable small subject adapter comprising at least one adapter surface smaller in size that the bed surface, an adapter interface that connects to the subject interface of the bed, and an adapter subject interface having an adapter anesthesia outlet, wherein the adapter anesthesia outlet is connected to the anesthesia outlet of the bed to supply anesthesia fluid from the bed to the removable small subject adapter. An adapter exhaust inlet proximate to the subject interface connects to the exhaust inlet to drain exhaust gas from the bed.

In embodiments, the subject imaging bed provides a chamber for the subject to be inserted in an imaging device. A temperature control mechanism uses radiant heating or cooling to control the temperature of the bed and the test subject. Embodiments also provide an anesthesia delivery mechanism placed in the vicinity of a nose cone, allowing the subject to receive the anesthesia localized near the mouth and nose. In embodiments, the bed also provides a scavenging system, allowing for a vacuum to remove the excess anesthesia from the chamber. This provides a convenient mechanism for the delivery and removal of anesthesia in only the nose cone area, thereby reducing the amount of fluid used in the subject imaging bed and sedating the subject during the scanning process.

To accomplish the foregoing and related ends, certain illustrative aspects of the claimed subject matter are described herein in connection with the following description and the annexed drawings. These aspects are indicative of various ways in which the subject matter may be practiced, all of which are intended to be within the scope of the claimed subject matter. Other advantages and novel features may become apparent from the following detailed description when considered in conjunction with the drawings.

A BRIEF DESCRIPTION OF THE DRAWINGS

The systems, devices and methods may be better understood by referring to the following description in conjunction with the accompanying drawings, in which like numerals indicate like structural elements and features in various figures. The components in the figures are not necessarily to scale, and simply illustrate the principles of the systems, devices and methods. The accompanying drawings illustrate only possible embodiments of the systems, devices and methods and are therefore not to be considered limiting in scope.

FIG. 2b is a top, detail view of an embodiment of the opposite end of the subject imaging bed depicted in FIG. 2a.

FIG. 3b is an alternate perspective view of the embodiment of the docking brace of FIG. 3a.

FIG. 4 is a bottom view of the embodiment of the docking brace of FIG. 3a.

FIG. 7b is a perspective view of the bottom of the small subject adapter shown in FIG. 7a.

FIG. 7c is a front view of an embodiment of the small subject adapter.

FIG. 7d is a top view of an embodiment of the small subject adapter.

FIG. 7e is a side view of an embodiment of the small subject adapter.

FIG. 9b is a top view of an embodiment of the subject imaging bed of FIG. 9a.

FIG. 10b is a top view of the docking brace of FIG. 10a.

FIG. 11b is a side view of the table stand of FIG. 11a.

DETAILED DESCRIPTION

Figure 1:
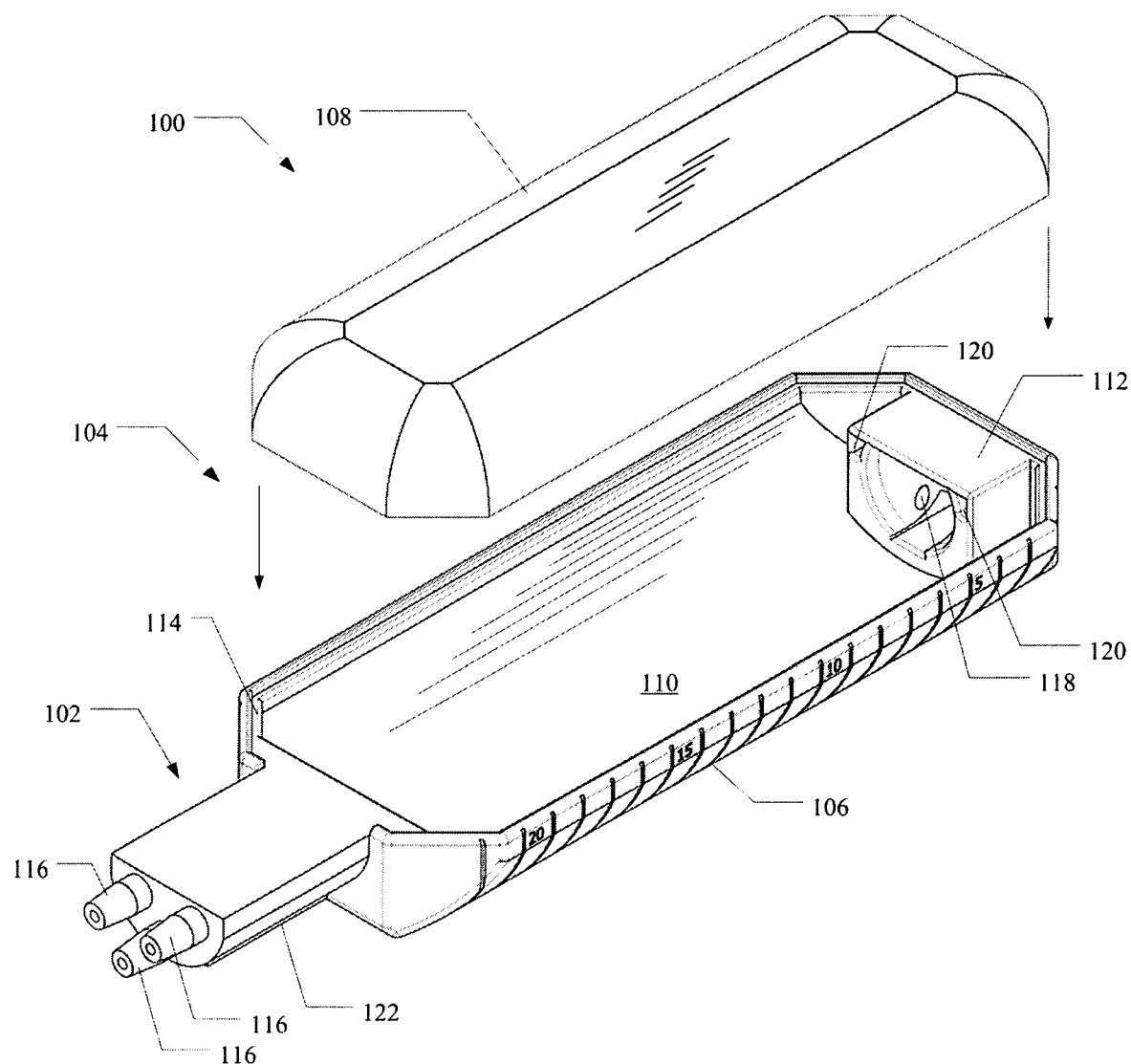
FIG. 1 is a perspective view of an embodiment of a subject imaging bed.

Aspects of the system and methods are described below with reference to illustrative embodiments. The references to illustrative embodiments below are not made to limit the scope of the claimed subject matter. Instead, illustrative embodiments are used to aid in the description of various aspects of the systems and methods. The description, made by way of example and reference to illustrative reference is not meant to being limiting as regards any aspect of the claimed subject matter.

Imaging beds described can be used for in vivo imaging of subjects. The beds can be used in conjunction with fluid sources and negative pressure to deliver a fluid, or mixture of fluids, such as an anesthetic gas, to one or more subjects. As used herein, "fluid" refers to a gas, vapor, liquid, or aerosol. The terms "subject imaging bed," "imaging bed," and "bed" are used interchangeably. In embodiments, the described imaging beds are used to deliver anesthetic gases or fluids, including but not limited to isoflurane, to sedate a subject or subjects for imaging.

When sedated, the subjects have a reduced capacity to regulate their body temperature, resulting in decreased blood flow and increased risk of hypothermia. This decreased blood flow is especially problematic when the target of imaging (e.g. a biomarker) relies on normal blood flow. Resistive heating elements can be used to aid subjects in maintaining a normal body temperature. Subjects can be enclosed in a chamber of the imaging bed to prevent excessive heat loss to the surrounding air and to minimize the likelihood of anesthetic gas reaching the atmosphere. However, resistive heating elements may introduce metal filaments in the imaging bed chamber, which interfere with production of clear images for many scanning techniques.

Generally, the subject will be sedated throughout the entire scanning period. To maintain sedation, anesthesia is continually delivered to the subject throughout the imaging procedure. To avoid over-sedation or suffocation, the chamber of the imaging bed can be connected to a vacuum line to draw out excess carbon dioxide and anesthesia gas as fresh air and additional anesthesia are delivered. During the imaging process imaging beds become saturated with anesthesia, and if the anesthesia is not properly exhausted, the anesthesia will remain in the chamber of the imaging bed after the conclusion of the imaging process. This results in potentially exposing lab workers to the anesthesia when the subject is removed from the chamber of the imaging bed. Repeated exposure to the anesthesia may have adverse health effects both on the subject and the lab worker. Further, flooding the entire imaging bed chamber with the anesthesia gas is an inefficient use of anesthesia, raising the costs of the imaging process.

In most imaging systems, the functional imaging space is limited. There is little room around the imaging bed when inserted in the imaging system. Therefore, any obstructions of this space are undesirable. Some systems use separate nose cones to deliver the anesthetic to the subject, which can increase the amount of functional space taken up by the anesthetic delivery system. Frequently, tubing is used alongside the imaging bed to provide the anesthetic to the nose cone. Additional tubing is used to exhaust or scavenge the anesthesia from the imaging bed. Tubes for anesthetic delivery and exhaust are unwieldy, awkward and add to the bulk of the imaging bed. Additionally, the tubing can be easily dislodged, creating multiple points of potential failure. Failure of the tubing can lead to insufficient anesthesia for the subject or leaking of the anesthetic into the lab atmosphere, potentially disrupting the imaging process and posing a potential health risk for the lab worker.

Embodiments of the subject imaging bed described herein utilize a compact and integrated nose cone and anesthetic delivery system to reduce the bulk and increase the amount of functional space of the imaging instrument that can be utilized. In addition, routing of fluids through the bed eliminate the need for external tubing, reducing potential failure points.

Additional embodiments of the imaging bed incorporate temperature control features that maintain the bed and subjects at a steady temperature during the imaging process. When sedated, the subjects have a reduced capacity to regulate their body temperature, resulting in decreased blood flow and increased risk of hypothermia. Decreased blood flow is especially problematic when the target of imaging (e.g. biomarker) is reliant on normal blood flow. Embodiments of imaging beds disclosed herein maintain the body temperature of the subject avoiding the detrimental effects of heat loss in the imaging subject.

Referring to FIG. 1, an embodiment of the subject imaging bed 100 includes a docking portion 102 and a base 106 in which a subject is placed for imaging. In the illustrated embodiment, the bed 100 includes a base 106 and a cover 108 that mates with the base 106 to form a chamber 104 and encapsulate the subject and contain anesthetic gas. In embodiments, the base 106 of the bed 100 is shaped and sized for insertion into an imaging system for scanning or imaging the subject positioned on the base 106. In embodiments, the subject rests on a bed surface 110 within the base 106 with the muzzle or nose of the subject positioned proximate to or within a nose cone or subject interface 112 through which the anesthesia is delivered to the subject.

In embodiments, the imaging bed cover 108 forms the top half of the chamber 104, enclosing the subject and anesthesia during the imaging process. In embodiments the cover 108 rests in a rabbet 114 in the upper surface of the base 106 to secure the cover 108 to the base 106. In other embodiments, the cover 108 is attached to the base 106 via a hinge or other mechanism that allows access to the bed surface 110 to insert or position the subject within the chamber 104. The chamber 104 is opened to insert, remove or access to the subject. In embodiments, the cover 108 and base 106 form a seal that prevents the anesthetic gas from escaping the chamber 104.

In other embodiments, the base 106 is used in subject imaging without the cover 108. The anesthetic gas is retained proximate to the subject interface 112 by an exhaust or scavenging system described below, which prevents the anesthetic gas from dissipating into the lab atmosphere. The cover 108 may serve to retain the subject within the chamber 104, should the anesthesia wear off sooner than predicted, and may assist in maintaining the temperature of the subject.

Figure 2A:
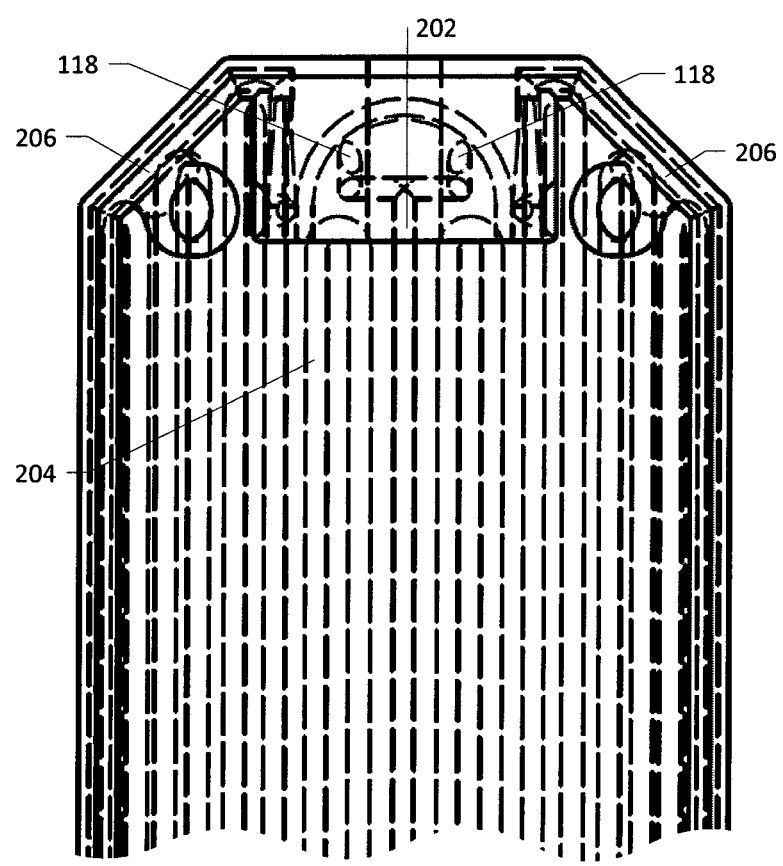
FIG. 2a is a top, detail view of an embodiment of an end of the subject imaging bed.
Figure 2B:
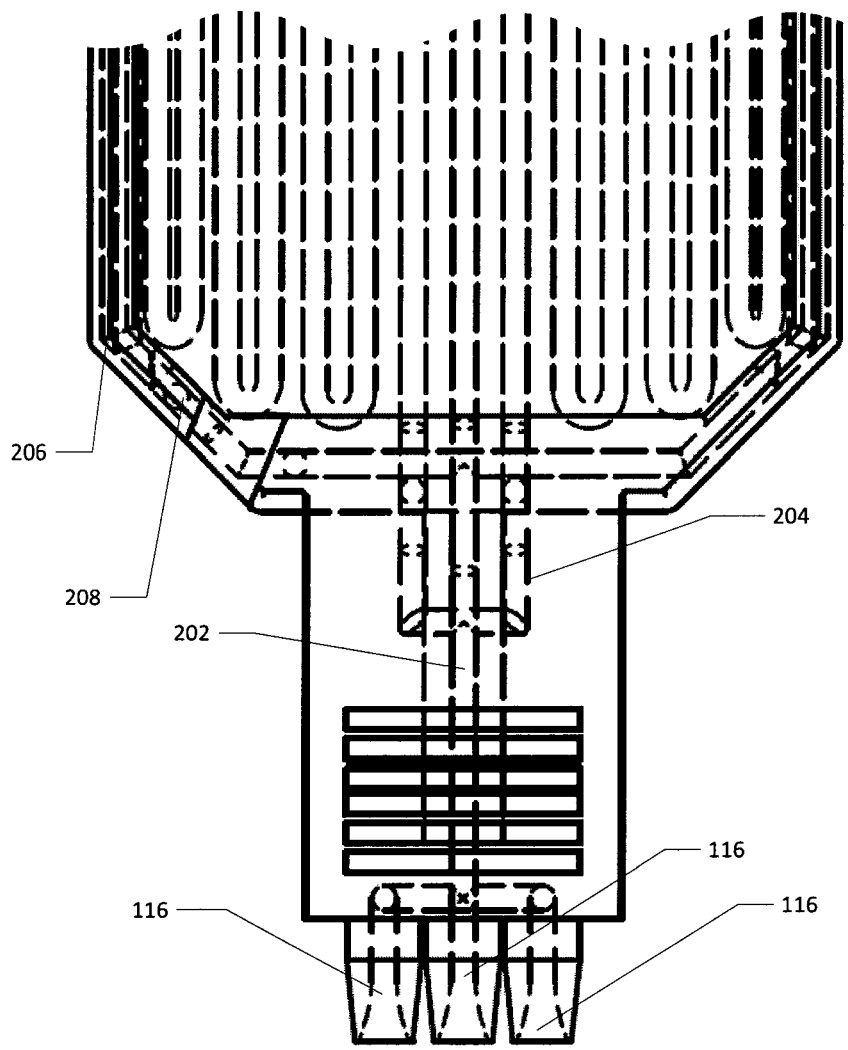

In embodiments, anesthesia fluid is pumped via a connector 116 through an anesthesia delivery channel 202 within the base 106, shown in FIGS. 2a and 2b, to an anesthesia outlet 118 in the subject interface 112. As used herein, the term "channel" denotes a conduit or connector and is not necessarily tubular in nature. In embodiments, the anesthesia delivery channel 202 provides fluid communication between the anesthesia outlet 118 and the connector 116, but is not necessarily implemented as a tube or pipe.

In embodiments, the bed surface 110 is heated or cooled by fluid, such as hot or cool air, pumped into the base 106 via a another connector 116 in the docking portion 102. The fluid or air and anesthesia are exhausted or scavenged through one or more exhaust inlets 120 and via one or more exhaust channels 206 in the bed 100. The fluid drawn through the exhaust inlets 120, which can be a mixture of anesthesia, air or other fluid, is referred to herein as exhaust fluid. The exhaust fluid is drawn out through a third connector 116 by application of a vacuum to the connector 116.

In embodiments, the connectors 116 are quick-connect mechanisms that allow bed 100 to be quickly and easily connected and disconnected to sources for a vacuum, fluid for heating or cooling, and anesthesia, such as via the docking brace 300, shown in FIG. 3a and described in further detail below. These connectors 116 facilitate preparing the bed 100 for insertion and removal from an imaging system, swapping out beds 100 inserted in the imaging system and speeding the process of imaging multiple subjects. As described in more detail below, the docking portion 102 can include one or more connecting guides 122 that facilitates aligning the docking portion 102 and the docking brace 300 for ease in attaching the docking portion 102 and the docking brace 300. The docking brace 300 can be attached to a support to hold the docking brace 300 and bed 100 in place during imaging process.

In embodiments, one or more of portions of the imaging bed 100 can be composed of materials transparent to the imaging technique of the imaging system. One or more portions of the imaging bed 100 can be made of chemically resistant plastics including, but not limited to, polyamides, polypropylene, polyethylene, and acrylics. Different materials may be used for different intended applications. For example, a common anesthetic is isoflurane, which degrades ABS and PLA plastics; accordingly portions of the imaging bed 100 can be made either in part or entirely of an acrylic or other chemically resistant material to resist chemical deterioration.

Referring to FIGS. 2a-2b, in embodiments the imaging bed 100 includes integrated pathways or channels through which anesthesia or other fluids can be delivered and exhausted from the bed 100, eliminating the need for separate tubing. As shown in FIGS. 2a and 2b, the imaging bed 100 can contain one or more cavities or channels 202, 204, 206 in the base 106. In the illustrated configuration of the channels 202, 204, 206, the anesthesia channel 202 extends the length of the bed 100 from the connectors 116 to terminate at the anesthesia outlets 118 within the subject interface 112. As shown, the anesthesia channel 202 can subdivide into multiple pathways to deliver anesthesia to the individual anesthesia outlets 118. Other embodiments may include different configurations of the anesthesia channel or channels 202 and the anesthesia outlet or outlets 118. For example, in other embodiments the anesthesia channel 202 is integrated into the sides of the base 106, or even the cover 108 of the imaging bed 100. An embodiment with the anesthesia channel 202 incorporated into the side of the base 106 is discussed in more detail below with respect to FIGS. 9a and 9b.

The incorporation of the anesthesia delivery channel 202 into the bed 100 eliminates the need for a separate tube to connect the subject interface 112 with the anesthesia source. This integrated anesthesia channel 202 makes it easier to insert and remove the imaging bed 100 from the imaging system, and reduces the potential for failures in the tubing or tubing connections. Consequently, the integrated anesthesia delivery apparatus is safer, more reliable and easier to use than imaging bed systems with external anesthesia tubing.

In the illustrated embodiment the base 106 includes an integrated temperature channel 204 adjacent to a substantial portion of the bed surface 110. Heated or chilled fluid travels via the temperature channel 204 through the majority of the interior of the base 106, heating or cooling the bed surface 110. In other embodiments, the base 106 is substantially hollow and the temperature channel 204 is implemented as a cavity within the base 106. Warm air or other fluids can flow through the temperature channel 204, transferring heat to the bed surface 110. This radiant heat maintains the bed surface 110 at a stable temperature, along with the subject positioned on the bed surface 110. In other embodiments, chilled air or fluids flow through the temperature channel 204, cooling the bed surface 110 and the subject. In an embodiment illustrated in FIG. 2b, the temperature channel 204 separates into two pathways each of which run the length of the base 106 before repeatedly doubling back upon themselves and substantially covering the separate halves of the base 106. After the fluid traverses the temperature channel 204 in the bed, the fluid flows out of one or more temperature control outlets 208 proximate to the docking portion 102 and is drawn into one or more exhaust inlets 120 proximate to the subject interface 112.

In embodiments, one or more exhaust channels 206 are integrated into the imaging bed 100. In the pictured embodiment, two exhaust channels 206, each extend along an edge of the base 106 of the bed 100. Each exhaust channel 206 is connected to an exhaust inlet 120 that scavenges anesthesia fluid and heated or cooled air into the exhaust channel 206. In embodiments, a vacuum is applied to the exhaust channel 206, directly or indirectly, to draw the anesthesia and fluid through the channel exhaust 206. In the illustrated configuration, the exhaust channel 206 connects to one or more exhaust inlets 120 before merging to a single pathway proximate to the docking portion 102.

Other embodiments may include different arrangements of the exhaust channels 206 within the base 106 or cover 108 of the bed 100. For example, the configuration of the anesthesia channel 202 and exhaust channels 206 can be reversed, such that the anesthesia channels 202 are located along the edge of the base 106, the exhaust channels 206 extend the length of the base 106 near the center of the base. Numerous configurations are possible to integrate the exhaust, temperature, and anesthesia channels 202, 204, 206 in the imaging bed 100.

The arrangement of temperature channels 204 within the bed 100 proximate to the bed surface 110 allows the user to control the temperature of the bed 100, without requiring the metal filaments typically used with resistive heating sources. In a resistive heating bed, metal wires or filaments would run through the base 106 of the chamber 104, where current would cause the filaments to radiate heat, raising the temperature of the bed surface and therefore the subject positioned on the bed surface 110. However, metal filaments can cause artifacts during imaging, which can reduce image accuracy and interfere with critical portions of an image. The use of temperature channels 206 negates the need for the filaments and eliminates potential imaging artifacts from such filaments. In addition, the temperature channels 206 can be used to cool the bed surface 110 as well, where resistive elements can only be used to heat. Typically, channels or cavities within the base 106 will not be apparent in images and have little or no effect on imaging and scanning.

Another advantage of the illustrated configuration is the generation of a flow of fluid or air from one or more temperature control outlets 208 down the length of the chamber 104 or base 106 to the exhaust inlets 120. The fluid is expelled from the temperature channels 204 via temperature control outlets 208 located opposite the subject interface 112. This fluid or air is pulled to the far end of the chamber 104 into the exhaust inlets 120 proximate to the subject interface 112. Consequently, the fluid is drawn across or past the subject positioned on the bed surface 110 and keeps the subject at the desired temperature. In embodiments, this flow of fluid works in conjunction with the heated or cooled bed surface 110 to maintain the temperature of the subject resting on the bed surface 110.

Positioning one or more exhaust inlets 120 proximate to the subject interface 112 can also help to limit the anesthesia fluid to a relatively small volume within or proximate the subject interface 112. In embodiment, little or no anesthesia is dissipated into the atmosphere, thereby reducing the exposure of lab workers to the fumes. Limiting the anesthesia to the area or volume proximate to the subject interface 112 during imaging also ensures that anesthesia will not interact with or be absorbed by the fur of the subject during the imaging process. Release of absorbed anesthesia or other gasses from the fur may result in adverse health effects in the subject or the lab researcher that handles the subject after the imaging process is complete.

In embodiments, the bed 100 can be quickly and easily mounted to a support apparatus through a docking brace 300. The docking brace 300 can be shaped and adapted to hold the imaging bed 100 and attachments to sources of anesthesia, fluid or a vacuum; while the support apparatus or arm holds the docking brace 300 and attached imaging bed 100 at the correct height an position for imaging. In some embodiments, the imaging bed connectors 116 are quick-connectors that insert into the matching connectors on the docking brace 300 without the need to separately connect tubing for anesthesia, heated or chilled fluid, or exhaust fluid. In an embodiment, the docking portion 102 of the bed 100 has three connectors 116, one each for anesthesia, heated or chilled fluid, and exhaust. As shown, these connectors 116 can be quick-connects that extend from the docking portion 102 distal from the chamber 104. These connectors 116 align with and engage three docking connectors 308 in a docking brace 300 (shown in FIG. 3a-3b) to form three connections. It will be appreciated by one having skill in the art that while the docking portion connectors 116 are illustrated as male connectors and the docking connectors 308 are shown as female connectors, the male and female connectors may be reversed, so that the docking portion 102 of the bed 100 has multiple female connectors that align with and engage male connectors in the docking brace 300 to form the three quick-connections.

Figure 3A:
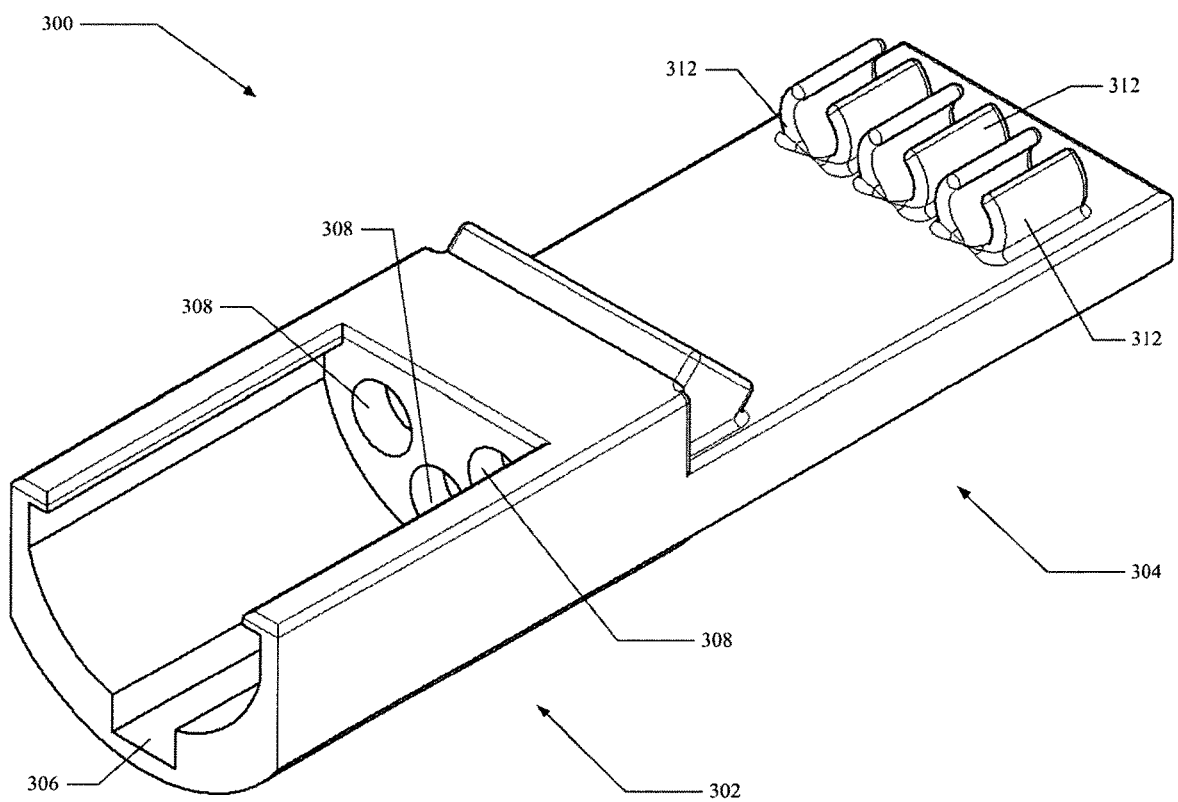
FIG. 3a is a perspective view of an embodiment of a docking brace.

Referring to FIG. 3a, an embodiment of a docking brace 300 is shown. The depicted docking brace 300 has a receiving portion 302 and a mounting portion 304. The mounting portion 304 serves as an attachment point to a support apparatus that holds the docking brace 300 in place during use. In embodiments, the receiving portion 302 is a sleeve, shaped complementary to the docking portion 102 of the bed 100. In embodiments, one or more alignment grooves 306 in the receiving portion 302 accepts one or more connecting guides 122 of the docking portion 102 of the bed 100, acting as a guide for insertion of the docking portion 102 and ensuring a quick and proper alignment between the docking portion 102 and receiving portion 302. In other embodiments, the key and groove configuration of the docking portion 102 and receiving portion 302 are reversed, so that the alignment groove is in the docking portion 102 of the bed 100 and the connecting guide is in the receiving portion 302 of the docking brace 300. Other embodiments may include multiple grooves 306 and connecting guides 122 pair. As discussed above, the receiving portion includes one or more docking connectors 308 that connect with the connectors 116 of the docking portion 102 of the bed 100 to supply fluids and a vacuum to the imaging bed 100.

Figure 3B:
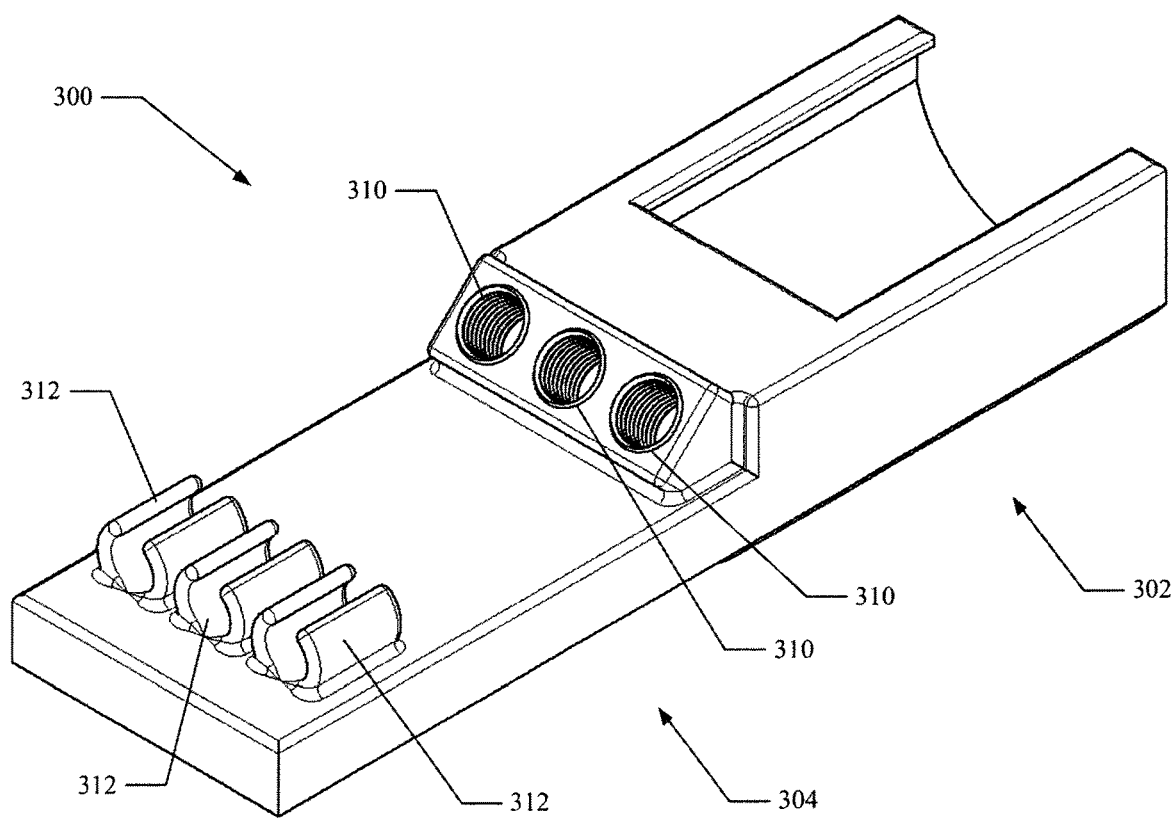

FIG. 3b shows an opposite view of the docking brace from FIG. 3a. The docking brace 300 comprises three external ports 310 which can be joined to sources for a vacuum, anesthesia, and a temperature control fluid. The external ports 310 are connected to the docking connectors 308. In certain embodiments, the mounting portion 304 of the docking brace 300 includes one or more tube clips 312 for conveniently securing tubes bringing warmed fluid and anesthesia to, or drawing exhaust fluid from, the external ports 310. Tube clips 312 can keep tubes organized and close to the docking brace 300, making it less likely that the tubes will be snagged, torn, kinked, or otherwise disturbed.

In a lab setting, the docking brace 300 can be connected to a support brace proximate to the imaging system. Anesthesia, temperature control fluid, and vacuum sources can each be connected to the one of the external ports 310 of the docking brace 300. When the researcher is ready to scan a subject, the imaging bed 100 with subject in place can be inserted into the docking brace 300. Upon insertion of the docking portion 102 into the receiving portion 302 of the docking brace 300, the imaging bed connectors 116 join with the docking connectors 308, connecting the imaging bed 100 to the anesthesia, fluid and vacuum sources.

Figure 4:
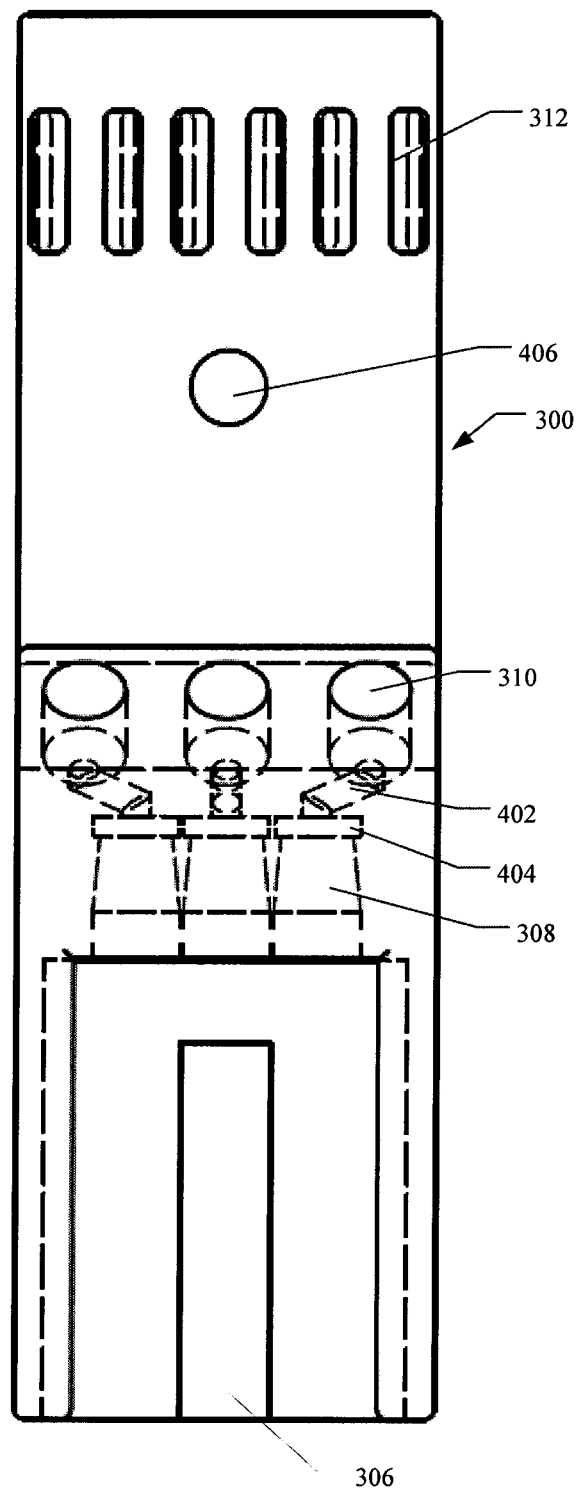

As shown in FIG. 4, the docking connectors 308 in the receiving portion 302 of the docking brace 300 are in fluid communication with external ports 310 on the mounting portion 304 of the docking brace via docking channels 402 through the interior of the docking brace 300. In certain embodiments, the external ports 310 are threaded to allow hose adapters to be conveniently installed. These allow the user to utilize hoses or tubes that are compatible with the typical lab workspace, without the added expense of acquiring new equipment or modifying other existing lab equipment. In embodiments, the docking connectors 308 include an O-ring 404. Including an O-ring 404 can enhance the seal between the docking connectors 308 and the imaging bed 116. Other embodiments contain an external brace attachment 406, allowing the user to attach the docking brace 300 to another object or support to stabilize the docking brace 300 in the imaging system and thereby reduce disturbances during the scanning process.

Figure 5A:
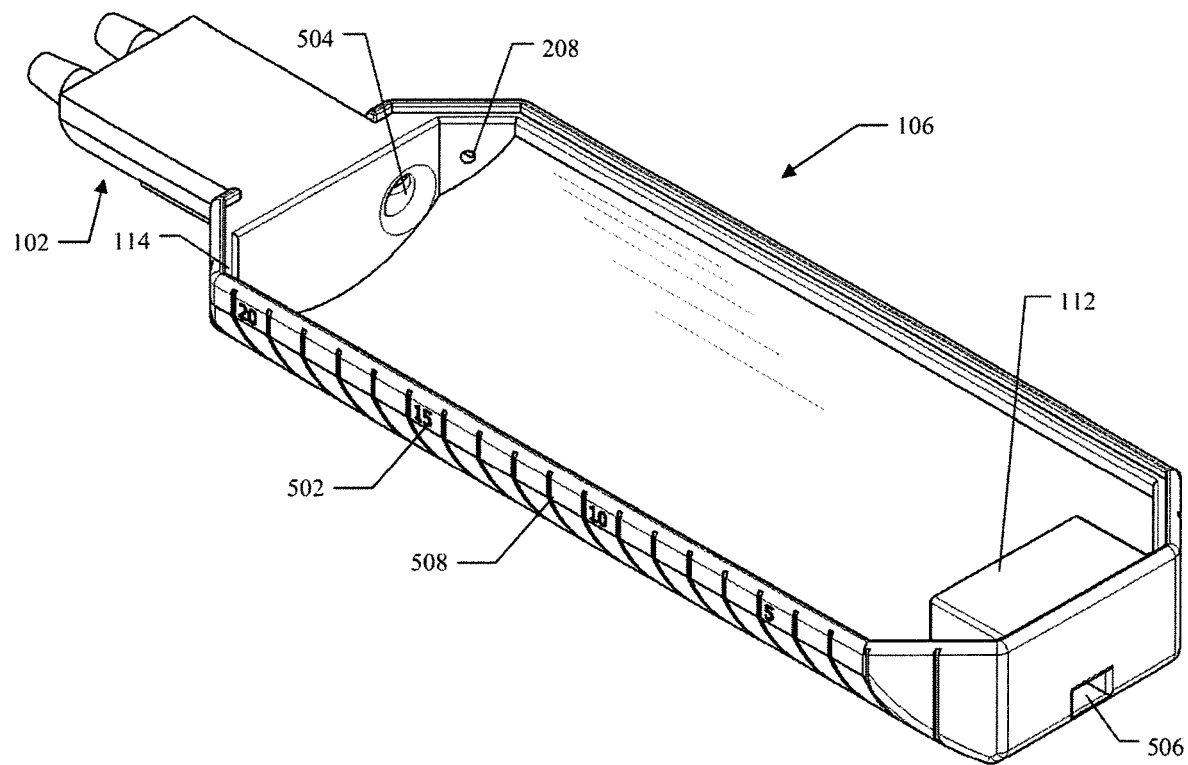
FIG. 5a is a perspective view of another embodiment of the subject imaging bed.

FIG. 5a shows another embodiment of the imaging bed 100, incorporating indicia 502 on the outer surface of the base 106 of the bed 100. Potential indicia 502 include, but are not limited to, subject positioning guides, and instrument depth guides, as well as a standard metric ruler. In embodiments, the bed 100 includes a tail aperture 504 located at the end of the base 106 opposite the subject interface 112. As illustrated, the tail aperture 504 is distal from the source of anesthesia within the chamber 104. Locating the tail aperture 504 opposite the subject interface 112 reduces the risk of anesthesia escaping into the atmosphere. Additionally, the flow of temperature control fluid within the chamber 104 from the temperature control outlets 208 to the exhaust inlets 120 decreases the risk of anesthesia escaping through the tail aperture 504. The tail aperture 504 can provide a more ergonomic placement of the subject's tail, positioned out of the way during imaging, and allowing the tail to act as a natural heat sink. In addition, the tail aperture 504 provides access to the tail veins of the subject without opening the chamber 104 or potentially without removing the imaging bed from the imaging system. In certain embodiments, the tail aperture 504 is a simple aperture in the wall of the base 106.

Figure 5B:
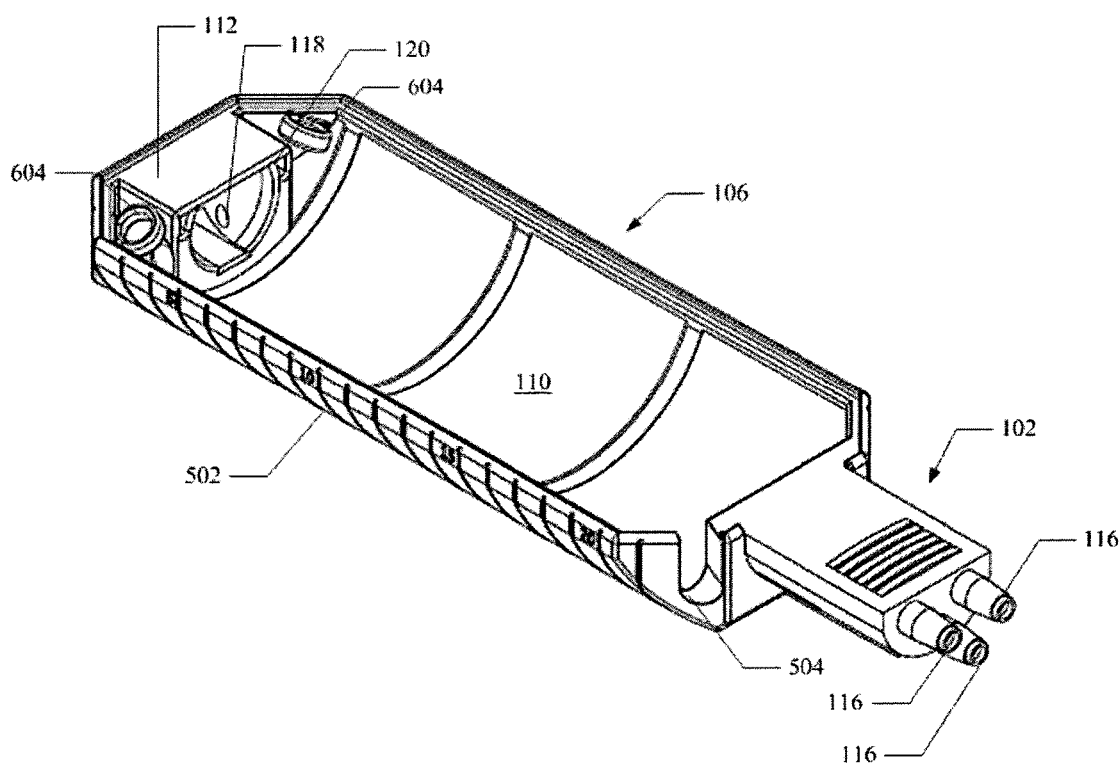
FIG. 5b is a perspective view of another embodiment of the subject imaging bed.

In another embodiment illustrated in FIG. 5b, the tail aperture 504 is a slot in the base 106 of the imaging bed 100. When inserting the subject in the base 106, the tail can simply be positioned in the slot 504. If a cover 108 is seated on top of the base 106, the attached cover 108 forms a boundary of the tail aperture 504.

In embodiments, the base 106 of the bed 100 can include surface features 508, such as ridges that improve grip when removing the bed 100 from the docking brace 300. While the surface features 508 are shown as ridges in the illustrated embodiments, it will be appreciated by one skilled in the art that other surface features 508 including, but not limited to, grooves, bumps, dimples, and knurling can be used.

In embodiments, the subject interface 112 includes an accessory interface 506 to receive an accessory device, such as a tooth bar 602 or small subject adapter 700, described in more detail below. In the illustrated embodiments, the accessory interface 506 extends through the wall of the chamber 104. In other embodiments, the accessory interface 506 extends only through the interior of the subject interface 112 and does not pierce the wall of the chamber 104.

Figure 6:
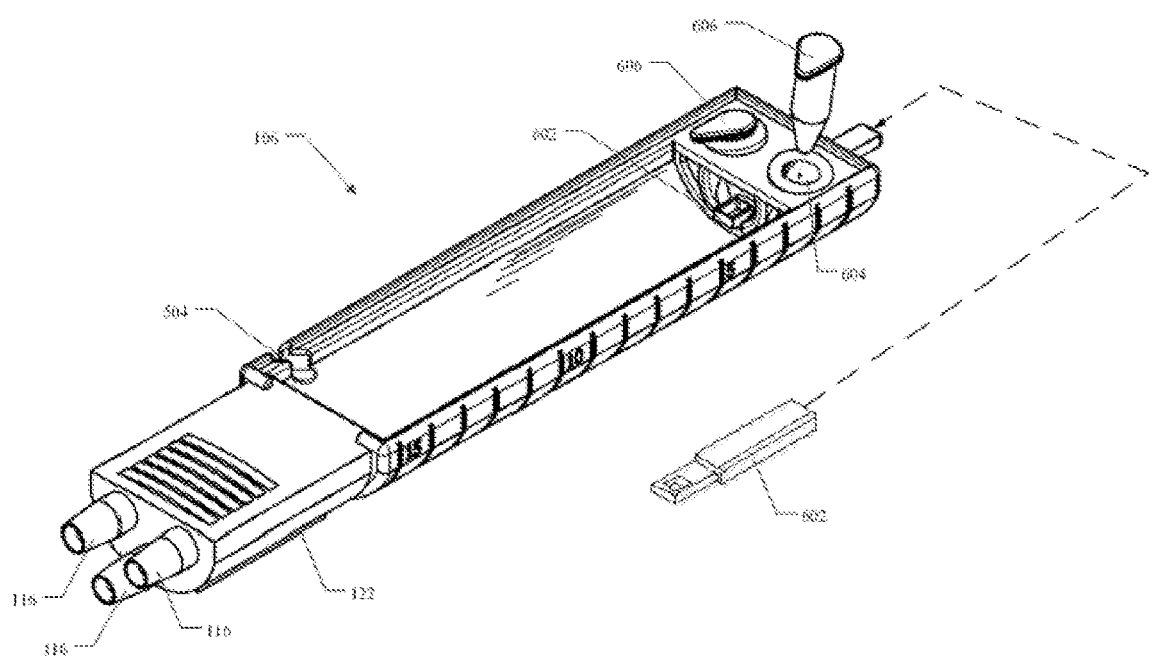
FIG. 6 is a perspective view of another embodiment of the subject imaging bed, incorporating fiducials.

As shown in FIG. 6, in embodiments, the imaging bed 100 includes one or more fiducial receptacles 604 shaped to receive fiducial markers. In embodiments, the fiducial receptacles 604 are shaped to receive fiducial containers 606, including, but not limited to, Eppendorf tubes. Such fiducial containers 606 can be loaded with fiducial markers and easily inserted or removed from the imaging bed 100. The illustrated embodiment shows the fiducial receptacles 604 positioned proximate to the subject interface 112. However, the fiducial receptacles 604 can be positioned at any convenient location in the base 106 or chamber 104. During imaging, fiducial markers can appear on the resulting image, allowing for calibration of the marker for later measurement. The use of removable fiducial containers 606 allows for the quick change of fiducial markers with the imaging bed 100—as may be required when using multiple imaging modalities—without disturbing the positioning of the subject or requiring cleaning of the bed 100 between uses. In embodiments, the fiducial receptacles 604 are cavities in the bed 100 into which the fiducial containers 606 can be inserted. In embodiments, the fiducial receptacles 604 comprise annular rings that can support a fiducial container 606, such as a microcentrifuge tube.

Figure 8:
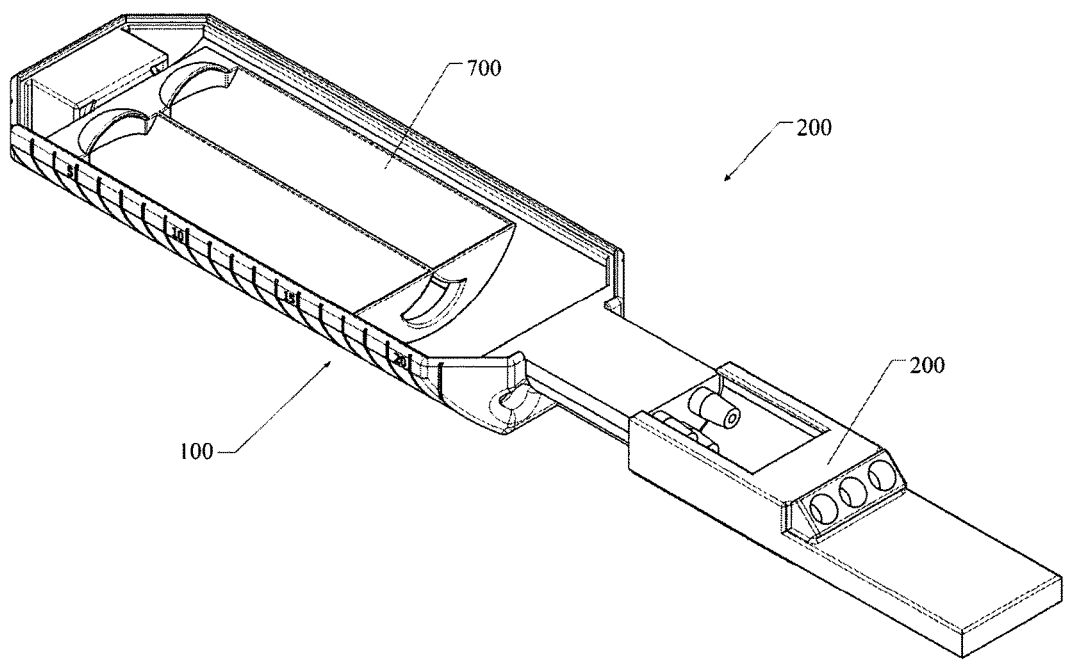
FIG. 8 is a perspective view of an embodiment of the subject imaging bed being inserted into an embodiment of a docking brace, assembled with an embodiment of a removable small subject adapter.

FIG. 6 also depicts a removable tooth bar 602 that assists in secure and consistent placement of the subject's head. The tooth bar 602 includes an aperture shaped to accept the subject's upper incisors so that the incisors are hooked over the bar 602 to secure and position the subject's head. This tooth bar 602 assists in maintaining the subject's muzzle proximate the subject interface 112 and ensuring delivery of anesthesia to the subject. Securing the subject's teeth reduces the possibility of the subject sliding within the imaging bed 100 and receiving insufficient anesthesia. As shown in FIG. 6, in embodiments, the tooth bar 602 can be removed to allow for insertion of a small subject adapter, as shown in FIG. 8.

Figure 7A:
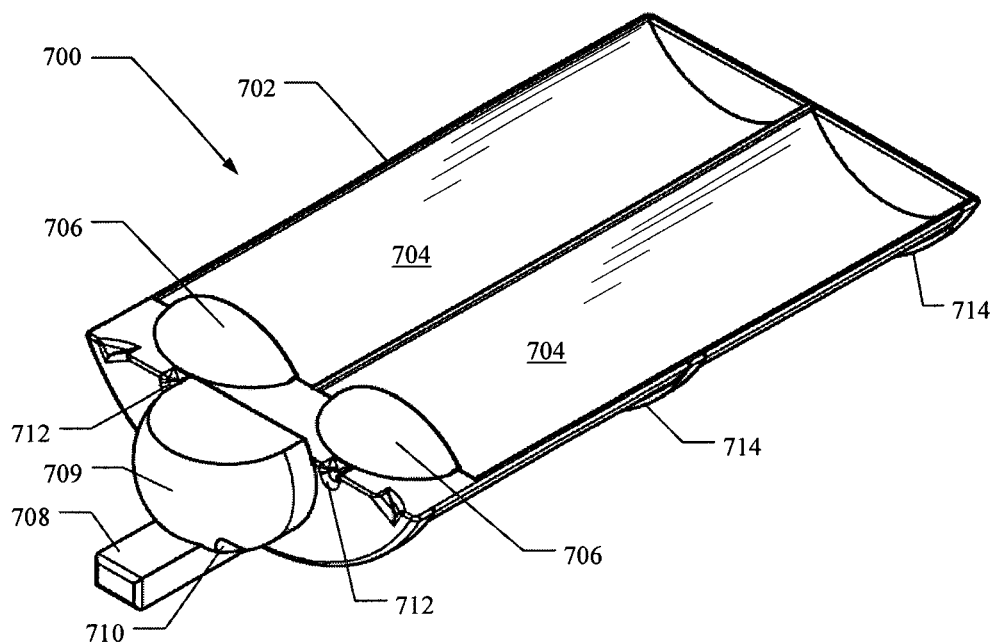
FIG. 7a is a perspective view of an embodiment of a small subject adapter.

Turning now to FIG. 7a, a small subject adapter 700 can be used to convert an imaging bed 100 into a bed 100 capable of supporting one or more small subjects. Using an adapter 700 for a single, smaller subject provides a better fit of subject in the bed 100 than resting the small subject in the relatively large imaging bed 100. Use of the adapter 700 can result in less potential movement of the subject and a clearer image. In another embodiment, the adapter 700 can be used to hold multiple subjects for simultaneous scanning. Imaging multiple subject at the same time reduces the overall time necessary to image a group of subjects, effectively increasing the throughput of the imaging procedure. Use of an adapter 700 with multiple subject also allows the user to create side by side comparisons of subjects in an image from a single scan.

As shown in FIG. 7a, in embodiments the small subject adapter 700 comprises an adapter bed 702, with one or more adapter surfaces 704 and one or more adapter subject interfaces 706. The adapter surfaces 704 provide platforms to support multiple subjects laid side-by-side. In embodiment, the adapter 700 substantially evenly channels anesthesia from the subject interface 112 of the imaging bed 100 to each of adapter subject interfaces 706 and to the small subjects within the adapter 700. As shown, individual adapter subject interfaces 706 are shaped to receive the nose or muzzles of the small subjects.

In embodiments, to seat the adapter 700 in the imaging bed 100, an adapter alignment rail 708 is inserted into the accessory interface 506 of the imaging bed 100 upon removal of the tooth bar 602. In an embodiment, when the adapter alignment rail 708 is slid into the accessory interface 506, an adapter interface 709 mates with the subject interface 112 of the imaging bed 100. One or more adapter anesthesia ports 710 in the adapter interface 709 align with the anesthesia outlets 118 within the subject interface 112 and accept anesthesia from the anesthesia outlets 118 of the imaging bed 100. As described in more detail with respect to FIGS. 7c and 7d, the adapter 700 channels anesthesia to multiple adapter subject interfaces 710 substantially evenly.

In embodiments, one or more adapter exhaust ports 712 connect to the exhaust inlets 120 of the imaging bed 100. These exhaust port 712 ensure the exhaust inlets 120 continue to draw anesthesia and air from the chamber 104 of the imaging bed 100 when the adapter 700 is in place in the bed 100. In embodiments, the adapter exhaust ports 712 are apertures or notches in the adapter 700 that ensure that the exhaust inlets 120 are not covered by the surface of the adapter 700 when the adapter 700 is in place within the base 106 of the bed 100.

Figure 7B:
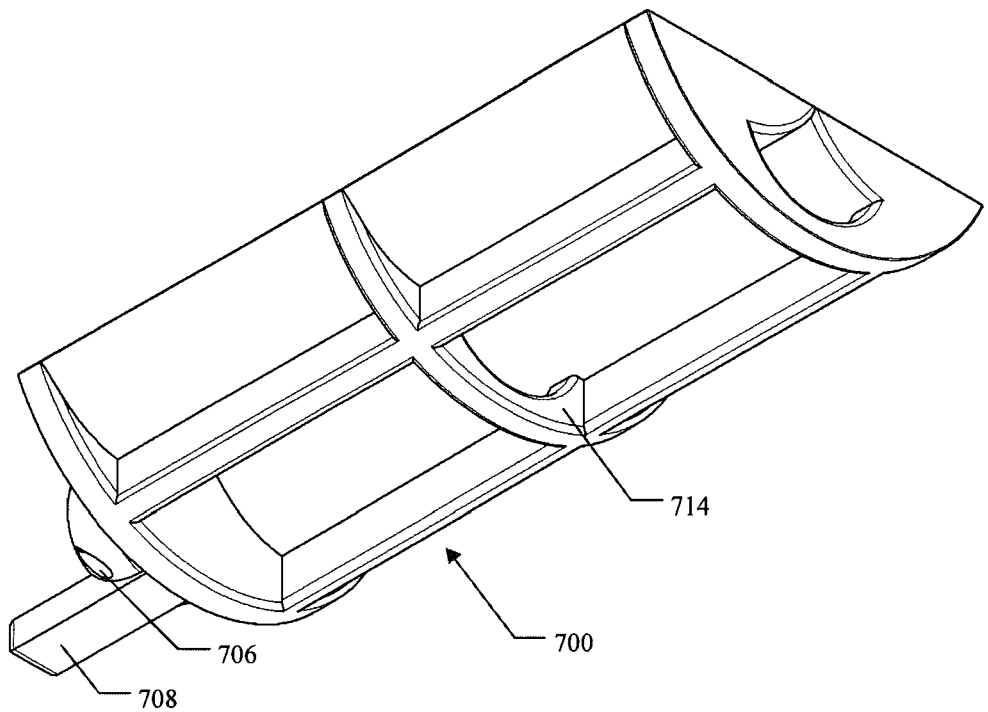

As shown in FIG. 7b, in embodiments, one or more stabilizing struts 714 keep the adapter surface 704 stable under the weight of the subjects. In the illustrated embodiment, the struts 714 are shown as U-shaped, but any structure suitable for bearing the weight of the subjects and keeping the adapter surface 704 stable can be used. In embodiments, the struts 714 serve to raise the adapter surface 704 slightly to compensate for the smaller size of the subjects.

FIGS. 7c-e depict front, top and side views of an embodiment of the adapter 700. In the illustrated embodiments, the adapter interface 709 is complementary in shape to the subject interface 112 and the alignment rail 708 is sized and shaped to mate with the accessory groove aperture 506. The adapter anesthesia ports 710 in the adapter interface 709 align with the anesthesia outlets 118 in the bed subject interface 112, and adapter anesthesia channels 716 extend from the adapter anesthesia ports 710 to adapter outlets 718 in the adapter subject interfaces 706. In use, with the small subject adapter 700 installed in the imaging bed 100, the anesthesia moves through the external anesthesia port 310 in the docking brace 300, through the docking channels 402 to the docking connectors 308. From there the anesthesia flows into the connector 116 of the imaging bed 100 and into the anesthesia channel 202 that extends the length of the bed 100, terminating at the anesthesia outlets 118 within the subject interface 112. From there, the anesthesia flows into the adapter anesthesia ports 706, through the adapter anesthesia channels 714, to the adapter anesthesia outlets 716 in the adapter subject interfaces 706. The flow of fluid is substantially evenly divided between adapter outlets 718 so as to expose all subjects to substantially the same level of anesthesia.

With the small subject adapter 700 in place, as illustrated in FIG. 8, the air flow across the imaging bed remains the same. Here, the anesthesia is emitted from one or more adapter subject interfaces 706. Temperature control fluid can travel through the base 106 of the imaging bed 100 and emerges from the temperature control outlets 208 at the opposite end of the base 106 from the adapter subject interfaces 706. Air flows from the temperature control outlets 208 across the subject to the exhaust inlets 120 and assists in maintaining the temperature of the subject.

FIG. 8 shows the subject imaging bed 100 partially assembled in the docking brace 300, with the small subject adapter 700 inserted into to the imaging bed 100. In embodiments, the entire imaging bed system 800 can be introduced into the chosen image scanning system. In embodiments, users can swap out the subject imaging bed 100 between scans and rapidly insert a new subject imaging bed 100 with a different test subject or subjects. In certain embodiments, there will be no need to individually disconnect and reconnect the anesthesia, temperature control fluid or vacuum sources to swap out the imaging bed 100. Instead, the first imaging bed is simply slipped out of the docking brace 300 and a second imaging bed is inserted into the docking brace 300. The connectors 116 reduce the time required to image multiple subjects and eliminate the need for users to individual disconnect and reconnect anesthesia, vacuum and temperature control fluid sources. This reduces the tediousness of repeated scanning tasks and the potential for connection failure and leaked anesthesia.

In use, the flow rate of the exhaust is typically adjusted to be about ten-fold greater than the flow rate of the anesthesia delivery at the anesthesia outlet. In lower fluid flow rate procedures, the flow rate of the exhaust is about five-fold greater than the flow rate of the anesthesia delivery at the outlet. In higher fluid flow rate procedures, the flow rate of the exhaust is about 15 to 20-fold greater than the flow rate of the anesthesia delivery at the anesthesia outlet.

Figure 9A:
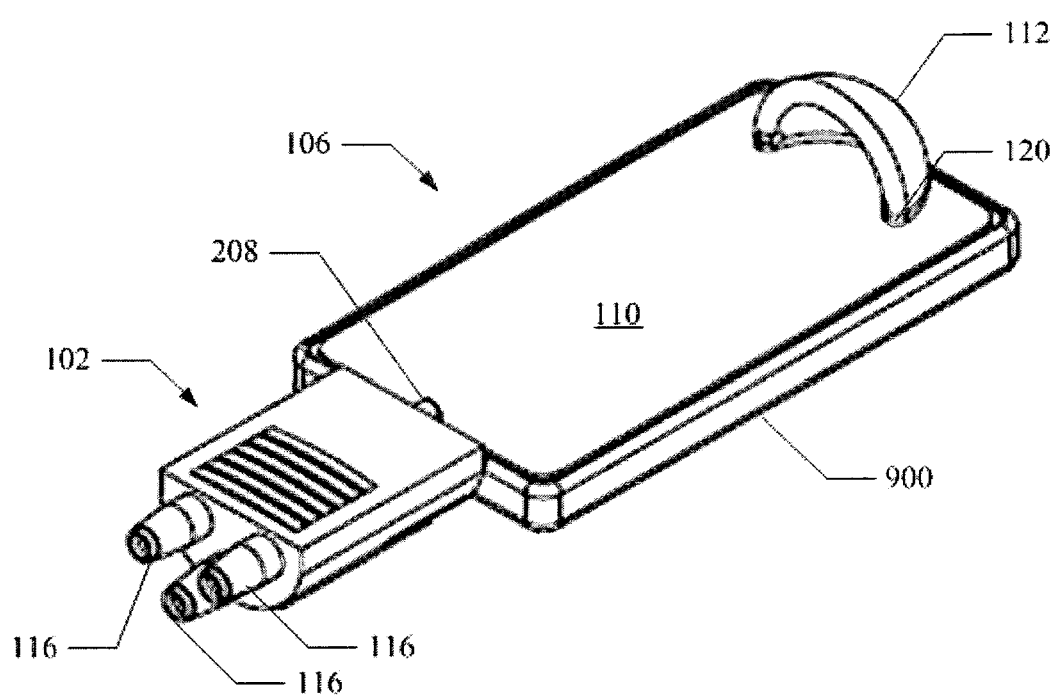
FIG. 9a is a perspective view of an embodiment of a subject imaging bed for use in optical imaging.
Figure 9B:
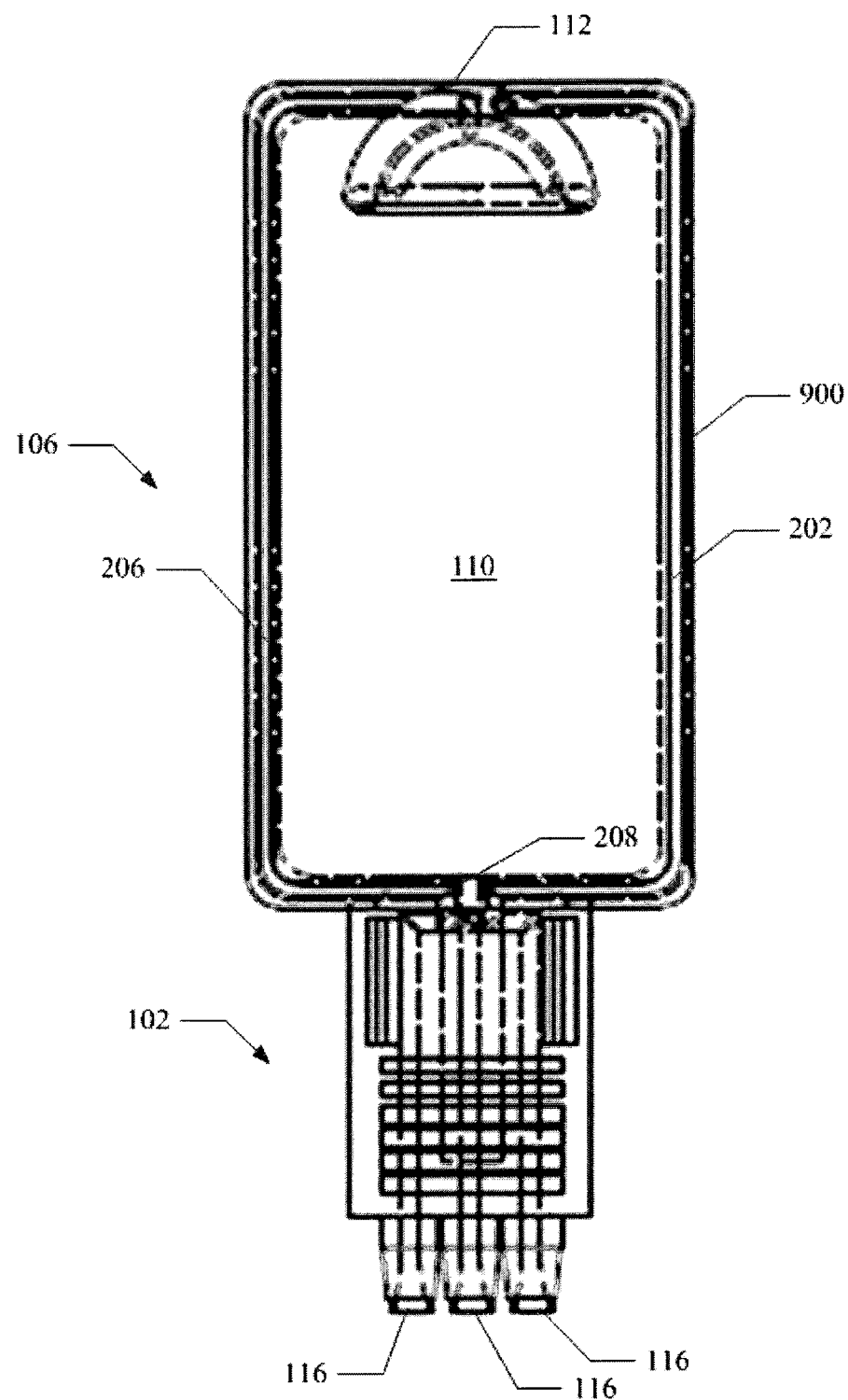

FIGS. 9a and 9b depict another embodiment of the imaging bed 100. Here, the bed surface 110 is generally flat and transparent. This embodiment of the bed 100 is particularly useful for optical imaging of the animal subject. This embodiment of the bed surface 110 allows the subject to be viewed or imaged through the bed surface 110 without obstruction. As illustrated, the anesthesia channel 202 and the exhaust channel 206 can be run through the sides or edges of the bed surface 110 and do not interfere with optical imaging through the bed surface. In this embodiment, the temperature channel 204 does not run through the bed surface 110 and instead can connect directly with the temperature control outlet 208. As with the previously disclosed embodiment, the heated or cooled fluid flows from the temperature control outlet 208 across the subject to the exhaust inlet 120 proximate to the subject interface 112, heating or cooling the subject depending upon the nature of the fluid.

Figure 10A:
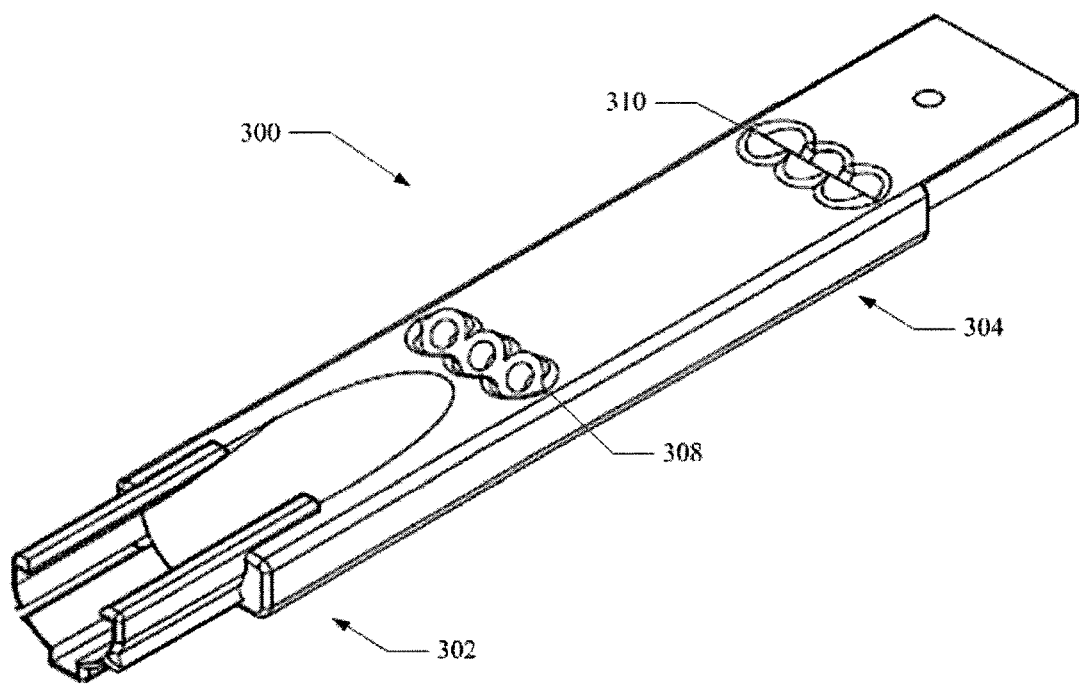
FIG. 10a is a perspective view of another embodiment of a docking brace.
Figure 10B:
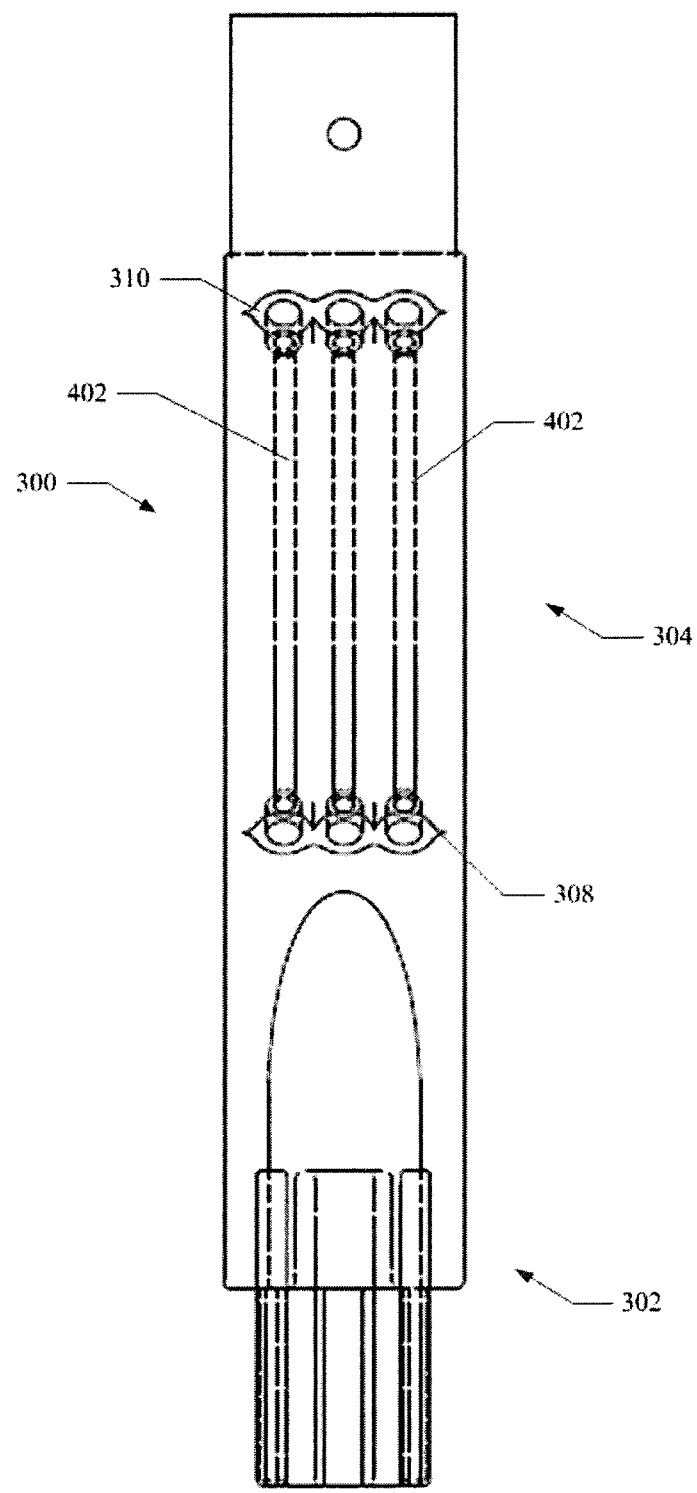

FIGS. 10a and 10b depict another embodiment of a docking brace 300. Here, the imaging bed 100 can be inserted into the curved receiving portion 302. A set of tubes or pipes can be attached to the imaging bed connectors 116 to connect the anesthesia, exhaust and temperature control fluid to the docking connectors 308. In an embodiment, quick connectors on the tubes or pipes can screw or plug into the docking connectors 308 to quickly connect or disconnect the imaging bed 100 from the docking brace 300. Interior docking channels 402 in the docking brace 300 connect to the external ports 310.

Figure 11A:
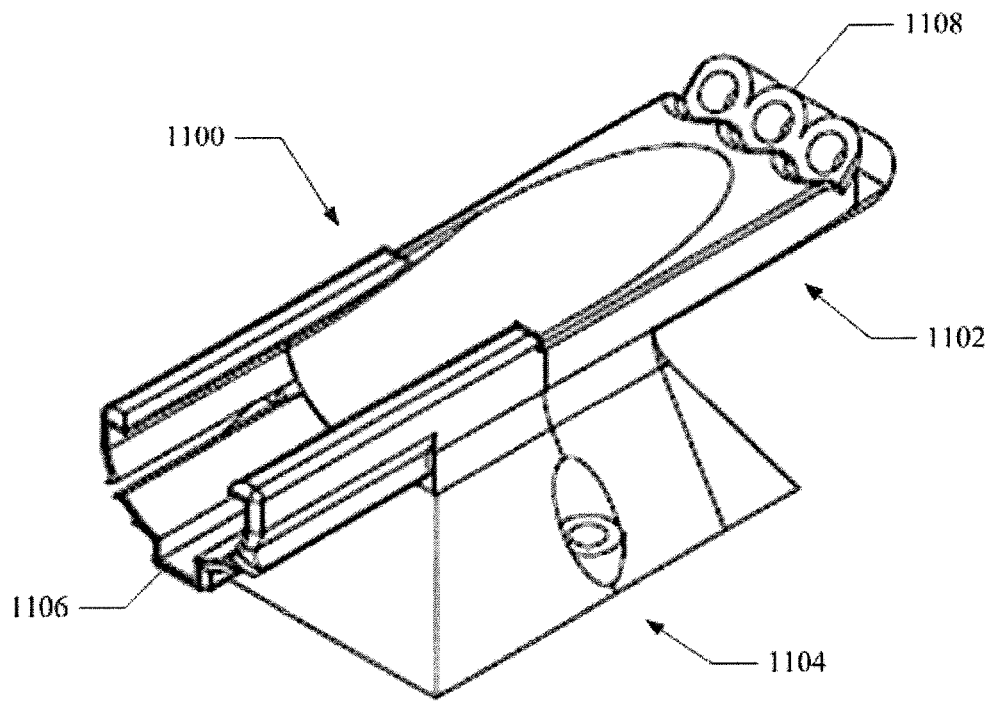
FIG. 11a is a perspective view of a table stand for use with an imaging bed.
Figure 11B:
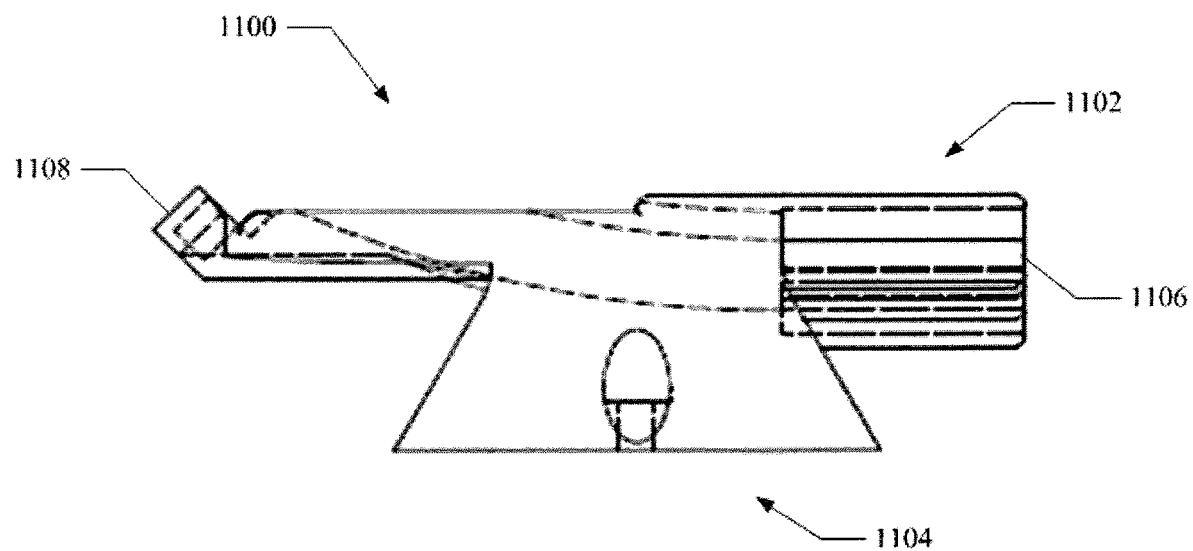

FIGS. 11a and 11b illustrate a table stand 1100 capable of supporting an imaging bed 100. The depicted table stand 1100 includes a mounting portion 1102 that receives the imaging bed 100 and a stand portion 1104 that rests upon a table or other support. In embodiments, the stand portion 1104 can be attached to a table surface, for example, the stand portion 1104 can be attached by one or more screws. In other embodiments, one or more portions of the table stand 1100 are formed from metal, or weighted so that the table stand 1100 remains stable. In other embodiments, the mounting portion 1102 can be similar to the docking brace 300, incorporating a table stand receiving portion 1106, with table stand connectors 1108.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has" or "having" or variations in form thereof are used in either the detailed description or the claims, such terms are intended to be inclusive in a manner similar to the term "comprising" as "comprising" is interpreted when employed as a transitional word in a claim.

What is claimed is:

1. A subject imaging bed, comprising:
a base that is configured to support a subject during imaging, the base having a bed surface on which a subject is configured to be positioned for imaging;
a subject interface connected to the bed surface, the subject interface having an anesthesia outlet;
an anesthesia channel integrated in the base that directs anesthesia fluid to the anesthesia outlet;
an exhaust inlet in the base located proximate to the subject interface;
an exhaust channel integrated in the base that connects to the exhaust inlet; and
a temperature channel integrated in the base and adjacent to a substantial portion of the bed surface, wherein the temperature channel directs a fluid to a temperature control outlet located substantially opposite the subject interface and exhaust inlet, wherein the temperature control outlet is oriented to direct flow of the fluid across the subject toward the exhaust inlet.

2. The imaging bed of claim 1, wherein the temperature channel substantially covers the length and breadth of the bed surface, wherein when the fluid is inserted into the temperature channel, the bed surface is heated by the flow of the fluid through the temperature channel.

3. The imaging bed of claim 1, further comprising a tail aperture in the base, the tail aperture located distal from the subject interface, wherein the tail aperture is configured to receive a tail of the subject to allow access to the tail during imaging.

4. The imaging bed of claim 1, further comprising a docking brace, wherein the docking brace comprises:
a connecting component that connects the docking brace to the base;
at least three connecting ports that receive a fluid source, an exhaust vacuum and an anesthesia fluid source; and
a support brace that secures the docking brace in position.

5. The imaging bed of claim 1, further comprising a fiducial receptacle in the base and shaped to support a removable fiducial container loaded with a fiducial marker.

6. The imaging bed of claim 1, further comprising a cover that mates with the base forming a chamber.

7. The imaging bed of claim 1, further comprising an accessory interface in the subject interface that accepts an accessory.

8. The imaging bed of claim 7, wherein the accessory is a tooth bar that is configured to secure a head of the subject.

9. The imaging bed of claim 7, wherein the accessory is a removable small subject adapter.

10. A subject imaging bed, comprising:
a base that is configured to support a subject during imaging, the base having a bed surface on which a subject is configured to be positioned for imaging;
a subject interface connected to the bed surface, the subject interface having an anesthesia outlet;
an anesthesia channel integrated in the base that directs anesthesia fluid to the anesthesia outlet;
an exhaust inlet in the base located proximate to the subject interface;
an exhaust channel integrated in the base that connects to the exhaust inlet; and
a temperature channel integrated in the base and adjacent to a substantial portion of the bed surface, wherein the temperature channel directs a fluid to a temperature control outlet located substantially opposite the subject interface and exhaust inlet; and
a docking brace, wherein the docking brace comprises:
a connecting component that connects the docking brace to the base;
at least three connecting ports that receive a fluid source, an exhaust vacuum and an anesthesia fluid source; and
a support brace that secures the docking brace in position.

11. The imaging bed of claim 10, wherein the connecting component comprises a plurality of quick-connect mechanisms that allow the base to be quickly connected and disconnected to sources for a vacuum, the fluid, and the anesthesia fluid.

12. The imaging bed of claim 10, wherein the connecting component is a sleeve, shaped complementary to a docking port of the bed.

13. The imaging bed of claim 10, the docking brace further comprising one or more tube clips for securing tubes supplying the anesthesia fluid, the fluid, or the exhaust vacuum.

14. The imaging bed of claim 10, wherein the at least three connecting ports are in fluid communication with the connecting component.

* * * * *